United States Patent
Patel

(10) Patent No.: US 11,826,466 B2
(45) Date of Patent: *Nov. 28, 2023

(54) BENDAMUSTINE SOLUTION FORMULATIONS

(71) Applicant: Navinta, LLC, Ewing, NJ (US)

(72) Inventor: Mahendra R. Patel, Delray Beach, FL (US)

(73) Assignee: Navinta, LLC, Ewing, NJ (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/111,041

(22) Filed: Dec. 3, 2020

(65) Prior Publication Data

US 2021/0169798 A1 Jun. 10, 2021

Related U.S. Application Data

(63) Continuation-in-part of application No. 15/689,895, filed on Aug. 29, 2017, now Pat. No. 10,905,677.

(60) Provisional application No. 62/381,906, filed on Aug. 31, 2016.

(51) Int. Cl.
| | |
|---|---|
| *A61K 31/4184* | (2006.01) |
| *A61P 35/02* | (2006.01) |
| *A61K 9/00* | (2006.01) |
| *A61P 35/00* | (2006.01) |
| *A61K 9/08* | (2006.01) |
| *A61K 47/18* | (2017.01) |
| *A61K 47/20* | (2006.01) |
| *A61K 47/10* | (2017.01) |

(52) U.S. Cl.
CPC ............ *A61K 9/08* (2013.01); *A61K 31/4184* (2013.01); *A61K 47/10* (2013.01); *A61K 47/20* (2013.01)

(58) Field of Classification Search
CPC ....... A61K 31/4184; A61K 47/18; A61K 9/08
See application file for complete search history.

(56) References Cited

U.S. PATENT DOCUMENTS

| | | | |
|---|---|---|---|
| 6,353,029 B1 * | 3/2002 | Parab | A61K 8/671 514/731 |
| 8,344,006 B2 | 1/2013 | Drager et al. | |
| 8,436,190 B2 | 5/2013 | Brittain et al. | |
| 8,445,524 B2 | 5/2013 | Courvoisier et al. | |
| 8,461,350 B2 | 6/2013 | Brittain et al. | |
| 8,609,707 B2 | 12/2013 | Palepu et al. | |
| 8,609,863 B2 | 12/2013 | Brittain et al. | |
| 8,669,279 B2 | 3/2014 | Cooper et al. | |
| 8,791,270 B2 | 7/2014 | Brittain et al. | |
| 8,883,836 B2 | 11/2014 | Cooper et al. | |
| 8,895,756 B2 | 11/2014 | Brittain et al. | |
| 9,000,021 B2 | 4/2015 | Sundaram et al. | |
| 9,034,908 B2 | 5/2015 | Sundaram | |
| 9,144,568 B1 | 9/2015 | Sundaram | |
| 9,265,831 B2 | 2/2016 | Palepu et al. | |
| 9,533,955 B2 | 1/2017 | Cooper et al. | |
| 9,572,796 B2 | 2/2017 | Palepu et al. | |
| 9,572,797 B2 | 2/2017 | Palepu et al. | |
| 9,572,887 B2 | 2/2017 | Sundaram | |
| 9,579,384 B2 | 2/2017 | Sundaram et al. | |
| 9,597,397 B2 | 3/2017 | Sundaram | |
| 9,597,398 B2 | 3/2017 | Sundaram | |
| 9,597,399 B2 | 3/2017 | Sundaram | |
| 9,603,930 B2 | 3/2017 | Patel | |
| 2013/0041004 A1 | 2/2013 | Drager et al. | |
| 2013/0210878 A1 | 8/2013 | Soppimath et al. | |
| 2013/0210879 A1 | 8/2013 | Palepu et al. | |
| 2013/0217888 A1 | 8/2013 | Shrawat et al. | |
| 2014/0024691 A1 | 1/2014 | Palepu et al. | |
| 2015/0087681 A1 | 3/2015 | Patel et al. | |
| 2015/0175554 A1 | 6/2015 | Shrawat et al. | |
| 2016/0158362 A1 | 6/2016 | Patel | |

FOREIGN PATENT DOCUMENTS

| | | |
|---|---|---|
| DE | 159289 A1 | 3/1983 |
| DE | 159877 A1 | 4/1983 |
| WO | 2014127802 A1 | 8/2014 |
| WO | 2015054550 A1 | 4/2015 |

OTHER PUBLICATIONS

Bendeka (bendamustine hydrochloride) injection, for intravenous use Initial U.S. Approval: 2008, 24 pages.
R.J.Sengwa, et. al, "Dielectric properties and hydrogen bonding interaction behavior in binary mixtures of glycerol with amides and amines", Fluid Phase Equililbria 266, (2008) 54-58.
European Patent Office, Search Report and Written Opinion for Application No. 17847529.9 (Year: 2019).
Florence Mottu, et al., "Organic solvents for pharmaceutical parenterals and embolic liquids: A review of toxicity data", PDA Journal of Pharmaceutical Science and Technology. Nov.-Dec. 2000;54(6):456-69. (1 page abstract only).
Package insert for Treanda® (Bendamustine hydrochloride) injection, for intravenous infustion. 6 pages.
Ribomustin® Bendamustine HCI product monograph, updated on Jan. 2002, http://www.ribosepharm.de/pdf/fibomustin_bendamustin/productmonograph.pdf. (30 page pdf. submitted).
Cezary M. Kinart, Wojciech J. Kinart, Adam Bald & Adam Szejgis (1995): Study of the Intermolecular Interactions in Liquid N,N-Dimethylacetamide-Water Mixtures, Physics and Chemistry of Liquids: An International Journal, 30:3, 151-157.

(Continued)

*Primary Examiner* — Jean P Cornet
(74) *Attorney, Agent, or Firm* — ST. ONGE STEWARD JOHNSTON & REENS LLC

(57) ABSTRACT

A ready to use or ready to dilute for use, stable liquid Bendamustine solution formed of 90 to about 200 mg/mL Bendamustine Hydrochloride or a hydrate form thereof, and a co-solvent consisting of 1% v/v to 12% v/v water and 88% v/v to 99% v/v N,N-Dimethylacetamide (DMA). The liquid Bendamustine solution is room-temperature stable for at least 90 days. Optionally, 0.01 to about 0.5 mg/mL antioxidant, preferably, butylated hydroxytoluene is included in the solution.

19 Claims, No Drawings

(56) References Cited

OTHER PUBLICATIONS

Treanda® (bendamustine hydrochloride) injection, for intravenous use Treanda® (bendamustine hydrochloride) for injection, for intravenous use Initial U.S. Approval: 2008, 20 pages.

* cited by examiner

BENDAMUSTINE SOLUTION FORMULATIONS

FIELD OF THE INVENTION

The present invention relates to liquid pharmaceutical formulations of Bendamustine Hydrochloride that exhibit long term stability at room temperature. The present invention also relates to methods of using the liquid Bendamustine formulations for the treatment of cancer.

BACKGROUND OF THE INVENTION

Bendamustine (Formula I) was initially synthesized in 1963 in the German Democratic Republic and was available under the name 'Cytostasan'.

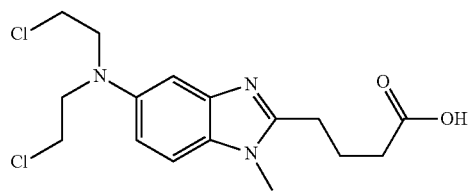

Formula I

Some of the main degradation impurities of Bendamustine are the monohydroxy compound (Formula II) and dihydroxy compound (Formula III) as well as dimer (Formula IV) in some instances.

administered to a patient as soon as possible after its reconstitution and reconstitution time should be short enough to reduce degradation." Anyarambhatla further teaches that room temperature storage can be convenient but is typically "not feasible" for an aqueous/organic mixture containing Bendamustine.

Bendamustine is used in the treatment of a number of cancers including leukemia, Hodgkins disease and multiple myeloma. Bendamustine is the active ingredient of the commercial product Treanda®, a lyophilized powder for reconstitution. The Treanda® product is supplied as a sterile non-pyrogenic lyophilized powder in a single-use sealed vial (e.g., 25-mg vial or 100-mg vial). Each 25-mg vial contains 25 mg of Bendamustine Hydrochloride and 42.5 mg of mannitol, USP. Each 100-mg vial contains 100 mg of Bendamustine Hydrochloride and 170 mg of mannitol, USP. The lyophilized powder is reconstituted just before its use with sterile water for injection. If particulate matter is observed after reconstitution then the injection is useless and is discarded. Lyophilized Bendamustine is also known in the art, as disclosed in e.g., U.S. Pat. Nos. 8,436,190 and 8,461,350.

Treanda® is also available as an IV solution 45 MG/0.5 ML and 180 MG/2 ML intended for intravenous infusion only after dilution with either 0.9% Sodium Chloride Injection, USP, or 2.5% Dextrose/0.45% Sodium Chloride Injection, USP. It is supplied as a sterile clear colorless to yellow solution in a single-dose vial at the concentration of 90 mg/mL of Bendamustine HCl. Each 0.5 mL vial contains 45 mg of Bendamustine Hydrochloride, 162 mg of Propylene Glycol, USP and 293 mg of N,N-Dimethylacetamide, EP.

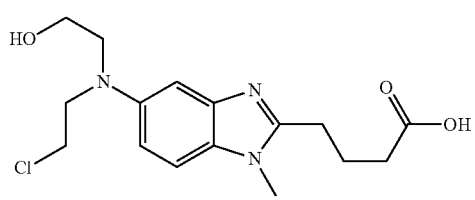

Formula II

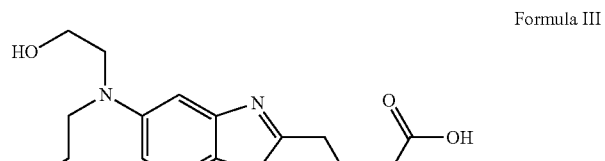

Formula III

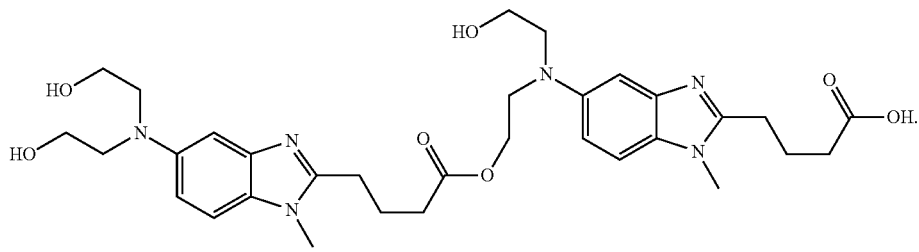

Formula IV

Historically Bendamustine was formulated as a lyophilized powder for mixture with water to form a solution at the time of use. Water is added to vials of lyophilized powder to form a Bendamustine solution The aqueous solution is not particularly stable and must be used within 30 min after reconstitution.

For example, International Patent Publication No. WO 2015/054550 to Anyarambhatla et al. (Luitpold Pharmaceuticals, Inc.) teaches pre-lyophilized liquid Bendamustine formulations. These formulations are then lyophilized, i.e. freeze dried to remove solvent and turn them solid. The solid then must be reconstituted (i.e., add solvent to dissolve a solid) before administration to a patient. Anyarambhatla teaches that that solutions, such as those claimed, "should be Each 2 mL vial contains 180 mg of Bendamustine Hydrochloride, 648 mg of Propylene Glycol, USP and 1172 mg of N,N-Dimethylacetamide, EP. An overfill of 0.2 mL is included in each vial.

More recently a liquid formulation of Bendamustine in a mixture of polyethylene glycol and propylene glycol has become commercially available and sold under the brand name Bendeka™. The Bendeka™ product is a 25 mg/ml solution of Bendamustine Hydrochloride which needs to be diluted with water before use. Each milliliter contains 25 mg of Bendamustine Hydrochloride, 0.1 mL of Propylene Glycol, USP, 5 mg of Monothioglycerol, NF, in Polyethylene Glycol 400, NF. Sodium hydroxide may be used to adjust the acidity of polyethylene glycol 400. It is commercially distributed by Teva Pharmaceuticals USA as a 100 MG/4 ML solution in 5 mL clear multiple-dose vials.

Since Bendamustine quickly degrades in aqueous solution, both the Treanda® and Bendeka™ products are prepared under anhydrous conditions by using an anhydrous form of Bendamustine or Bendamustine salt and anhydrous solvent(s). But solid anhydrous Bendamustine Hydrochloride is pharmaceutically unstable, as disclosed in U.S. Pat. No. 8,669,279. Thus, use of anhydrous Bendamustine Hydrochloride in formulation requires special handling during storage and manufacturing operations.

There have been many efforts to prepare a stabilized Bendamustine solution proposed in the prior art.

For example, solutions of Bendamustine HCl in water free Propylene Glycol in presence of inert gas have been reported in German Patent No. 159289. It was also reported that the solution had reasonable stability. German Patent No. 159289 discloses details of an injectable solution of Bendamustine. German Patent No. 159877 (DE) discloses a method for preparing 4-[1-methyl-5-bis(2-chloroethyl) amino-benzimidazolyl-2)-butyric acid.

Ribomustin® Bendamustine HCl product monograph, updated on January 2002, http://www.ribosepharm.de/pdf/ribomustin_bendamustin/productmonograph.pdf, provides information on Ribomustin®, including product description.

In U.S. Pat. No. 8,344,006, a Bendamustine HCl formulation is prepared by solubilizing the drug in N,N-Dimethylacetamide and Propylene Glycol. It shows that a solution of Bendamustine in propylene glycol significantly degrades upon standing at room temperature but a solution in N,N-Dimethylacetamide is relatively stable. The preferred formulation uses Bendamustine HCl in 66% N,N-DMA and 34% propylene glycol. Drager et al. teaches Bendamustine converts to non-Bendamustine products (i.e., "degrades") upon exposure to certain nucleophiles, for example, water. From the data presented in the patent, it may be inferred that Propylene Glycol is required to make a pharmaceutically acceptable Bendamustine solution.

Another liquid formulation of Bendamustine is disclosed in U.S. Pat. No. 8,609,707. This patent describes a Bendamustine HCl liquid formulation prepared by solubilizing the drug in Polyethylene Glycol and Propylene Glycol. The patent discloses that the stability of the resulting formulation is improved by adding an antioxidant.

Bendamustine is poorly soluble in Polyethylene Glycol alone. There is also a risk of freezing and precipitation of the drug product at or below room temperature because the melting point of Polyethylene Glycol is near room temperature. Therefore, a small amount of Propylene Glycol is required to mitigate the issue. The resulting formulation is limited by the low solubility of the drug in the solvent mixture. Higher concentration of Propylene Glycol would improve the solubility at the expense of formulation stability and therefore this approach is not desirable.

Both the solution formulations in U.S. Pat. Nos. 8,344,006 and 8,609,707 require the use of propylene glycol. Both of the patents require strictly anhydrous conditions to avoid degradation of the drug. Accordingly, an anhydrous form of Bendamustine HCl is required for the formulation. However, even with the non-aqueous formulations, significant degradation was observed from the reaction between the drug and solvent molecules. One or two glycol esters of Bendamustine are formed during storage of the formulations. U.S. Patent Application Publication No. 2013/0210879 discloses typical impurities formed from a mixture of propylene glycol and Bendamustine.

U.S. Patent Application Publication No. 2013/0041004 discloses a non-aqueous liquid Bendamustine formulation wherein the solvent system comprises of a polar aprotic solvent DMA and a polar protic solvent selected from alcohol, propylene glycol or glycerin, and antioxidant, wherein the solvent system may contain up to 34% of propylene glycol.

U.S. Patent Application Publication No. 2016/0158362 discloses a Bendamustine composition in which Bendamustine is stabilized in a solvent system comprising DMA and glycerin, wherein glycerin takes about 5% v/v to about 60% v/v. One advantage of this Bendamustine composition is that it can tolerate the water molecules in the hydrate form of a Bendamustine or its salt and may contain additional (up to 1%) of water while maintaining a stable Bendamustine formulation.

U.S. Patent Application Publication No. 2013/0210878 to Kumaresh Soppimath et al. (Innopharma, Inc.) discloses stability results of Bendamustine formulations that are allegedly ready-to-use. The solutions contain an aqueous portion having significant quantities of sodium chloride, and only provide stability data for up to 7 days. Storage at room temperature yield unacceptable levels of impurity. The assay results and degradation of such products is significant. The product is not commercially viable.

To be a commercially saleable pharmaceutical product that is ready to use or ready to dilute liquid formulation, the formulation must able to be manufactured, sold to a wholesaler and/or hospital and stored for a commercially practical amount of time before the product is distributed to caregivers for administration to a patient in need thereof. A product stored at room temperature is always a preferred formulation for ease of handling compared to product stored at 2-8° C.

The United States Pharmacopeia monograph for Bendamustine Hydrochloride for Injection suggests the limit of monohydroxy impurity (designated as Bendamustine related compound E) is up to 1.5% and total the impurities in the product is 3.5%. Linear extrapolation of Soppimath et al.'s formulations at room temperature will fail at 3 months.

The currently approved and marketed liquid drug products TREANDA® and BENDEKA® must be stored and transported under refrigerated condition between 2-8° C. (36-46° F.).

There exists a need for concentrated and stable liquid Bendamustine formulations that have better stability and improved impurity profile and ease of use than the previously disclosed formulations. It is desired to provide a stable liquid Bendamustine product which reasonably tolerates a small amount of moisture or water content. In particular, it is desired to have liquid Bendamustine formulations that exhibit long term stability at room temperature. It is also desired that the liquid Bendamustine product can be easily manufactured by using a readily available and stable hydrate form of Bendamustine or its salt. It is further desired that the liquid Bendamustine product utilizes a simple solvent system, for example, by using a single solvent alone or with water, to provide liquid Bendamustine products with good stability.

SUMMARY OF THE INVENTION

To achieve at least some of the foregoing objectives, the present invention provides stable Bendamustine-containing liquid formulations, preferably where Bendamustine may be derived from one of the hydrated forms of the pharmaceutically acceptable salt, most preferably by using a monohydrate form of Bendamustine Hydrochloride suitable for pharmaceutical use. The liquid formulations are stable for long term storage at room temperature.

The present invention further provides methods of producing such liquid Bendamustine formulations. The pharmaceutical formulations can be used for any condition that is sensitive to treatment with Bendamustine, such as neoplastic diseases.

In one embodiment, the invention comprises a pharmaceutically acceptable liquid Bendamustine composition comprising about 10% w/v Bendamustine Hydrochloride or a hydrate thereof and a cosolvent consisting of about 1% v/v to about 12% v/v water and about 88% v/v to about 99% v/v N,N-Dimethylacetamide (DMA), wherein the composition is substantially free of sodium chloride and/or polyols, and wherein the liquid composition is ready for use for up to 3 months at room temperature storage conditions without the need to lyophilize or ready for further dilution for up to 3 months at room temperature storage conditions without the need to lyophilize.

In some preferred embodiments, the formulation includes a stabilizer, such as an antioxidant. In preferred embodiments, the stabilizer is present at about 0.001% w/v to 0.05% w/v, more preferably 0.005% w/v to about 0.05% w/v of the formulation. In particularly preferred embodiments, the stabilizer is an antioxidant. Most preferably, the stabilizer is butylated hydroxytoluene.

In certain embodiments, the composition includes about 20 to about 200 mg/mL Bendamustine Hydrochloride or a hydrate form thereof. In some of these embodiments, the composition includes about 60 to about 200 mg/mL Bendamustine Hydrochloride or a hydrate form thereof. In some of those embodiments, the composition comprises about 80 to about 180 mg/mL Bendamustine Hydrochloride or a hydrate form thereof. In other preferable embodiments, the composition comprises about 90 to 200 mg/mL Bendamustine Hydrochloride or a hydrate form thereof. In especially preferred embodiments, the formulation contains about 100 mg/mL Bendamustine Hydrochloride or a hydrate form thereof.

In particularly preferred embodiments, the Bendamustine composition is filled into a container with nitrogen and sealed.

In another aspect, the invention provides a room temperature-stable, liquid Bendamustine formulation consisting essentially of about 90 to about 200 mg/mL Bendamustine Hydrochloride or a hydrate form thereof, about 0.01 mg/mL to about 0.5 mg/mL antioxidant, more preferably about 0.05 mg/mL to about 0.5 mg/mL antioxidant, and a co-solvent consisting of about 1% v/v to about 12% v/v water and about 88% v/v to about 99% v/v N,N-Dimethylacetamide (DMA), wherein the formulation is ready for use for up to 3 months at room temperature storage conditions without the need to lyophilize or ready for further dilution for up to 3 months at room temperature storage conditions without the need to lyophilize. The formulation contains no less than about 98% of the amount of the Bendamustine Hydrochloride or a hydrate form thereof upon analysis by HPLC at initial testing and after 3 months at room temperature.

In preferred embodiments, the formulation contains about 100 mg/mL Bendamustine Hydrochloride or a hydrate form thereof.

In certain preferred embodiments, the Bendamustine Hydrochloride or a hydrate form thereof is Bendamustine HCl monohydrate.

In some embodiments, the cosolvent consists of about 2% v/v to about 6% v/v water. In certain preferred embodiments, the cosolvent consists of 3% v/v water and 97% v/v DMA.

In some embodiments, the antioxidant concentration is about 0.05 mg/mL. In other embodiments, the antioxidant concentration is about 0.018 mg/mL. In yet other embodiments, the antioxidant concentration is about 0.5 mg/mL.

In certain preferred embodiments, the antioxidant is butylated hydroxytoluene.

In some advantageous embodiments, the co-solvent is degassed with nitrogen.

In yet another aspect, the invention comprises a pharmaceutically acceptable, sealed vial consisting of about 10% w/v Bendamustine Hydrochloride or a hydrate thereof; about 0.001% w/v to about 0.05% w/v antioxidant; more preferably about 0.005% w/v to about 0.05% w/v antioxidant, a cosolvent consisting of about 1% v/v to about 12% v/v water and about 88% v/v to about 99% v/v N,N-Dimethylacetamide (DMA); and nitrogen.

In some embodiments, the vial comprises about 0.0018% w/v antioxidant. In other embodiments, the vial comprises about 0.05% w/v antioxidant. In yet other embodiments, the vial comprises about 0.5% w/v antioxidant.

In certain preferred embodiments, the antioxidant is butylated hydroxytoluene.

In some embodiments, the cosolvent consists of about 2% v/v to about 6% v/v water and about 94% v/v to about 98% v/v DMA. In some preferred embodiments, the cosolvent consists of about 3% v/v water and about 97% v/v DMA.

In certain embodiments, the Bendamustine Hydrochloride or a hydrate thereof is Bendamustine Hydrochloride monohydrate.

DETAILED DESCRIPTION OF THE INVENTION

The present invention provides liquid pharmaceutical formulation of Bendamustine comprising Bendamustine active pharmaceutical ingredient dissolved in N,N-Dimethylacetamide and water in an amount of about 0.3% to 40%, preferably about 1-12% water, more preferably about 1-8% water, most preferably about 2-6% water. The source of Bendamustine in the formulation may be Bendamustine free base, its pharmaceutically acceptable salts, and/or various hydrate forms. Preferably, the pharmaceutical composition includes Bendamustine Hydrochloride. More preferably, the pharmaceutical composition includes Bendamustine Hydrochloride monohydrate.

The compositions herein are substantially free of sodium chloride and/or polyols. When used herein, "substantially free" means that no sodium chloride or polyols have been added to the composition. Compositions that are substantially free of a material does not preclude small amounts of such materials being present in a composition, which may occur from impurities in intentionally added ingredients or may be formed by in situ reactions of intentionally added ingredients.

Polyols is meant to include simple hydroxyl compounds, such as glycerin, and a number of polyethers of polyols and polyesters, such as propylene glycol, polyethylene glycol.

Compared to anhydrous Bendamustine Hydrochloride, Bendamustine Hydrochloride monohydrate is a better choice to be used in the preparation of Bendamustine liquid formulations. As stated previously, anhydrous Bendamustine HCl is unstable and may convert to hydrates upon storage in a solid form. In contrast, Bendamustine Hydrochloride monohydrate has a better impurity profile than anhydrous Bendamustine Hydrochloride and is more readily accessible in pure form (e.g., without residual solvents). Bendamustine Hydrochloride monohydrate may be used directly to prepare a ready for use or ready for further dilution pharmaceutical formulation without the need to lyophilize Bendamustine HCl prior to the formulation.

The liquid Bendamustine formulations of the present invention have a high concentration of the drug (i.e., Bendamustine, its salt and/or hydrate thereof) with very good stability and improved impurity profile. The novel liquid Bendamustine formulations of the present invention may also be easily prepared by a simple process.

Aqueous solutions of Bendamustine are not very stable and all the prior work in making a solution formulation of Bendamustine was aimed at using non aqueous solvents where Bendamustine dissolves easily and does not generate impurities on storage. Generally, an anhydrous form of Bendamustine was used to prepare these prior art solutions.

It is reported in U.S. Pat. No. 8,344,006 that solubility of Bendamustine Hydrochloride in DMA is about 56 mg/mL at room temperature. We have found that Bendamustine Hydrochloride hydrate has a solubility of about 65 mg/mL at 2-8° C. We observed that one can routinely make solutions of Bendamustine Hydrochloride monohydrate in DMA containing up up to about 200 mg/mL by adding water to DMA.

A solution of 90 mg/mL of Bendamustine Hydrochloride hydrate in DMA did not develop any precipitate when stored at 2-8° C. for five months. Surprisingly, a solution which contains about 0.5% water was stable at 5° C. up to 3 months with less than 2% degradation. Subsequently, we found that solutions of Bendamustine Hydrochloride hydrate in DMA containing up to about 40% water are stable for up to 9 months at 5° C. These observations allowed us to prepare pharmaceutical dosing solutions of Bendamustine Hydrochloride hydrate in DMA with or without additional water. Liquid formulations containing water were observed to have long term stability at room temperature.

All % of solvents herein refer to volume %, unless otherwise specified. The term "% v/V" (also written as "v/v %") means the volume of a solute in the total volume of solution. As one skilled in the art would understand, when the solute is a liquid, sometimes it is convenient to express its concentration in volume/volume percent. The calculation of "% v/v" is:

Concentration solute (v/v %)=volume solute (mL)/
Total volume of solution (mL)×100

As used herein, the term "about" is defined as ±10%, preferably ±5%.

Based on an actual or calculated weight of Bendamustine free base in the pharmaceutical formulation (regardless whether the source of Bendamustine is a Bendamustine salt and/or hydrate form), the active pharmaceutical ingredient (i.e., Bendamustine, a pharmaceutically acceptable salt, and/or a hydrate form thereof) is in an amount of about 20 to about 200 mg/mL; preferably, in an amount of about 40 to 200 mg/mL or 90 to 200 mg/mL; more preferably, in an amount of about 60 to 180 mg/mL; even more preferably, in an amount of about 60 to 150 mg/mL. In particularly preferred embodiments, the liquid formulation comprises about 100 mg/mL or 10% w/v of Bendamustine HCl.

Solutions of Bendamustine in N,N Dimethylacetamide with up to about 40% water provide superior drug solubility and stability of Bendamustine in the resulting solution. Without wishing to be bound by theory, it is believed that the reason for less reactivity and hence the stability of Bendamustine solution in DMA, even in presence of water, is due to significant hydrogen bonding in solution. It has been reported that a stable hydrogen bonded complex is formed between one molecule of DMA and two molecules of water. This mole ratio of DMA and water corresponds to 29% water by weight based on the total weight of water and DMA. It is believed that the hydrogen bonding between DMA, Bendamustine and water could be responsible for better stability of the formulation. As a result, the formulation of the present invention can even tolerate the presence of up to about 40% water. In some embodiments, it tolerates about 10% of water; in other embodiments, it tolerates about 20% of water in further additional embodiments, it tolerates about 25% of water. In some other embodiments, it tolerates about 25% to about 40% of water. The liquid formulations have surprisingly long term stability at room temperature when a co-solvent of DMA and 0.5-12% water is used.

In certain particularly preferred embodiments, Bendamustine HCl is dissolved in a DMA:water co-solvent wherein the volume ratio of DMA:water is 88:12 to 99:1, most preferably 97:3. In certain of those embodiments, the co-solvent is degassed.

The present formulations do not require sodium chloride or polyols and are able to achieve greater solubility than previous formulations containing DMA with salt and/or polyols.

In certain preferred embodiments, an antioxidant can be included and will not adversely affect the stability of the Bendamustine solutions at room temperature storage. It has been found that, in certain embodiments in which about 1% v/v to about 12% v/v water are used with about 88% v/v to about 99% v/v DMA, addition of a stabilizer, such as an antioxidant, improves the long term stability at room temperature. Antioxidants such as butylated hydroxytoluene may prevent reaction of DMA or impurities contained therein with oxygen and prevent the creation of oxidizing species that may affect the stability of the product.

As used herein, stabilizer refers to, without limitation, antioxidant, chelating agent, preservative, buffering agent, pH adjusting agent or combination thereof. For purposes of this application, stabilizer does not include sodium chloride and/or polyols.

Antioxidants can include ascorbic acid, sodium bisulfate, thiourea, butylated hydroxytoluene (BHT), tocopherols, and amino acids. In particularly preferred embodiments the antioxidant is BHT.

When included, the amount of stabilizer can range from 0.001% w/v to 1.0% w/v, more preferably about 0.005% w/v to about 0.05% w/v. In certain embodiments, the amount of stabilizer is about 0.005% w/v. In other embodiments, the amount of stabilizer is about 0.05% w/v. In yet other embodiments, the amount of stabilizer is about 0.0018% w/v.

In certain embodiments, an amount of stabilizer/antioxidant can be added to a liquid formulation at a concentration of about 0.01 mg/mL to about 1.0 mg/mL, more preferably about 0.05 mg/mL to about 0.5 mg/mL. In certain embodiments, the concentration of stabilizer/antioxidant is about 0.05 mg/mL, about 0.018 mg/mL or about 0.5 mg/mL.

Analysis of the liquid formulations of the present invention can be performed using techniques known in the art, including, for example, HPLC, gas chromatography, and NMR. After exposure to typical commercial storage conditions, analysis of the formulations of the present invention will indicate that the formulation contains no less than about 90% of the amount of Bendamustine present prior to exposure to the storage conditions. Preferably, analysis will indicate that the formulation contains no less than about 95% of the amount of Bendamustine present prior to exposure to the storage conditions. More preferably, analysis will indicate that the formulation contains no less than about 98% of the amount of Bendamustine prior to exposure to the storage conditions.

Storage conditions refers to those long term, intermediate and accelerated conditions discussed in ICH guidelines for stability testing of active pharmaceutical ingredients and finished pharmaceutical products (WHO 2009), the contents of which is incorporated herein by reference. Namely, storage conditions include 5° C.±3° C., 25° C.±2° C./60% RH±5% RH, 30° C.±2° C./65% RH±5% RH, and 40° C.±2° C./75% RH±5% RH. As used herein, storage of compositions refers to storage within a container closure system.

In preferred embodiments of the present invention, analysis of the formulations of the present invention will indicate that the formulation contains no less than about 90% of the amount of Bendamustine present prior to exposure to storage conditions that include temperatures of about 5° C. and time periods of about 30 days (about 1 month) to about 365 days (about 1 year). Preferably, analysis of the formulations of the present invention will indicate that the formulation contains no less than about 90% of the amount of Bendamustine present prior to exposure to storage conditions that include temperatures of about 5° C. and time periods of about 30 days (about 1 month), about 90 days (about 3 months), about 180 days (about 6 months), and about 240 days (about 9 months). Preferably, analysis will indicate that the formulation contains no less than about 95% of the amount of Bendamustine present prior to exposure to storage conditions that include temperatures of about 5° C. and time periods of about 30 days (about 1 month) to about 365 days (about 1 year). More preferably, analysis will indicate that the formulation contains no less than about 95% of the amount of Bendamustine present prior to exposure to storage conditions that include temperatures of about 5° C. and time periods of about 30 days (about 1 month), about 90 days (about 3 months), about 180 days (about 6 months), about 240 days (about 9 months), and about 365 days (about 1 year).

The solutions of Bendamustine Hydrochloride hydrate prepared according to this invention may be diluted or constituted with 0.9% Sodium Chloride in water, or 5% Dextrose in water to obtain a dosing solution suitable for intravenous dosing to a patient. An important advantage of this invention is that one may prepare a much higher concentration of Bendamustine in DMA than other mixed solvent systems reported in prior art. Since the drug has a higher concentration in the present invention, the patient will be exposed to less amounts of organic solvents for a given dose of the drug.

Liquid formulations of the present invention are stable over the course of a typical commercial storage period. Typical commercial storage conditions include time periods of, for example, about 30 days, about 90 days, about 180 days, and about 365 days (about 1 month, about 3 months, about 6 months, and about 1 year). Typical commercial storage conditions also include temperatures of about 25° C. (ambient room temperature) and refrigerated temperatures below ambient room temperature, for example, about 5° C. Preferably, the liquid formulations of the present invention are stored at refrigerated temperatures but can, advantageously, be stored at room temperature for much longer than previous products.

As used herein, "stable" is defined as no more than a 10% loss of Bendamustine and the presence of no more than about 3.5% of total impurities after storage for a minimum of three months at room temperature conditions. Preferably, formulations of the present inventions will have no more than a 10% loss of Bendamustine, more preferably, no more than a 5% loss of Bendamustine, under typical commercial storage conditions. An advantage of the present formulations, is that they show improved stability over prior Bendamustine formulations. That is, they show less than 2% loss of Bendamustine under typical storage conditions.

Another aspect of this invention is that, in this process, Bendamustine HCl monohydrate, which is accessible in pure form without any residual solvents, can be used directly in the formulation. Another benefit is that there is no need to lyophilize Bendamustine HCl as a means of purification prior to the formulation.

Bendamustine HCl monohydrate can be prepared by the method disclosed in Journal of Practical Chemistry, 1963, 178-186, the contents of which are incorporated herein by reference. Compared to Bendamustine HCl anhydrous, the use of Bendamustine HCl monohydrate has the following advantages. Bendamustine HCl monohydrate has a better impurity profile and is more readily accessible in pure form without residual solvents. Thus, it can be used directly in the formulation of a pharmaceutical composition ready for administration. Also, as noted earlier, the anhydrous Bendamustine HCl is pharmaceutically very unstable and converts to the hydrate form upon storage. The degradation of Bendamustine HCl is mainly caused by hydrolysis of the chloride of Bendamustine and formation of ester from the carboxylic group of Bendamustine with individual solvents. In alcoholic solvents such as methanol or ethanol, Bendamustine is easily converted to methyl or ethyl ester at room temperature. By using the preferred solvent mixture of DMA and water disclosed in the present invention, only trace amounts of impurities are formed.

Currently available United States pharmacopeia monograph for Bendamustine Hydrochloride for Injection suggests a limit of 0.6% for related compound D and monohydroxy impurity (designated as Bendamustine related compound E) up to 1.5%. The total impurities limit in the product is 3.5%.

A further important feature of the presently disclosed formulations is they do not produce any solvent derived ester impurities. Moreover, the major degradation impurity is not a new chemical entity that requires additional safety testing. The principal impurity in certain formulations of the present invention is a known metabolite of Bendamustine.

An embodiment of the invention is a pharmaceutical liquid composition of Bendamustine HCl monohydrate, preferably containing not more than 2% of Bendamustine monohydroxy impurity when stored under a refrigerated condition (2 to 8 degrees C.) or room temperature for an extended period of time.

As used herein, an "extended period of time" means 9 months or greater.

Another embodiment of the invention is a liquid formulation of Bendamustine containing not more than about 2%, preferably less than 1%, of Bendamustine polar impurity when stored under refrigerated condition or room temperature or an extended period of time.

A further embodiment of the invention is a process for manufacturing a liquid formulation of Bendamustine HCl that controls Bendamustine degradation impurities during the process such that the total concentration of all Bendamustine impurities in the final product is less than about 4.0% under refrigerated storage or room temperature for an extended period of time.

Another embodiment of the invention is a liquid formulation of Bendamustine containing not more than about 2%, preferably less than 1%, of Bendamustine polar impurity when stored under refrigerated condition or room temperature for an extended period of time.

It is preferred that the solutions be filled into a vial or a syringe with a suitable stopper, or an ampule. Most preferably, the solutions are contained in a USP type 1 amber vial and closed with a coated stopper. The primary packed product can be further packed into a suitable carton.

In a preferred method of manufacture, the Bendamustine solution is filled into a primary container and purged with nitrogen for at least 90 minutes. In certain embodiments, the solution is purged with nitrogen for not less than 90 minutes.

EXPERIMENTS

HPLC Procedure for Analysis of Bendamustine Formulations:
Solvent A: Water:MeCN (acetonitrile):TFA (trifluoroacetic acid) (90:10:0.1)
Solvent B: Water:MeCN:TFA (50:50:0.1)
UV: 230 nm
Flow rate: 1.0 mL/min
Column: Symmetry C-18 (250×4.6 mm) 5 μm, or equivalent
Column temp: 25° C.
Sample temp: 5° C.
Injection volume: 10 μL
Run time: 53 min
Diluent: Methanol HPLC Gradient:

| Time(min.) | % A | % B |
|---|---|---|
| 0.01 | 100 | 0 |
| 18 | 50 | 50 |
| 30 | 45 | 55 |
| 40 | 35 | 65 |
| 41 | 10 | 90 |
| 43 | 100 | 0 |
| 53 | 100 | 0 |

Sample preparation: Dilute the solution with methanol to prepare a sample with concentration of 1 mg/mL for injection directly in to HPLC. It may be necessary to perform a second dilution to reach a targeted sample concentration.

Results: Percent of each Bendamustine related compound is calculated against average peak area of Bendamustine HCl low level working standard using an equation below:

$$\% \text{ impurity} = \frac{Ru}{Rs} \times \frac{\text{Standard Concentration}}{\text{Sample Concentration}} \times 100\% \times 1000$$

where Ru is area of the impurity peak and Rs is area of the standard peak

TABLE

HPLC Retention Times and Structures of Bendamustine Impurities

| Sr No | Name of Impurity | RT (min) | RRT | Structure |
|---|---|---|---|---|
| 1 | Deschloroethyl Bendamustine | 13.8 | 0.55 | 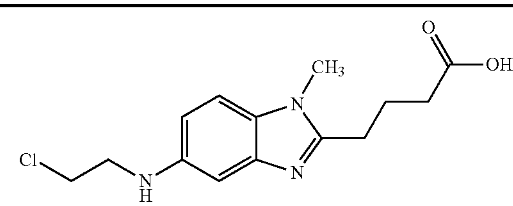 |
| 2 | Monohydroxy Bendamustine | 14.5 | 0.58 | 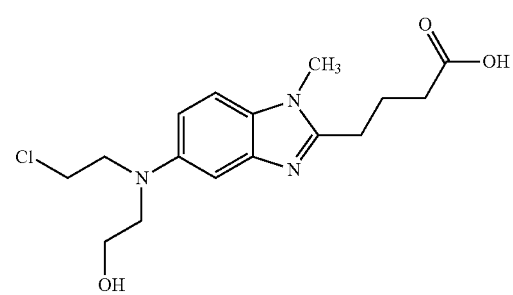 [SMILES: Cn1c(CCCC(=O)O)nc2cc(N(CCO)CCCl)ccc21] |
| 3 | Bendamustine methylester | 31 | 1.24 | 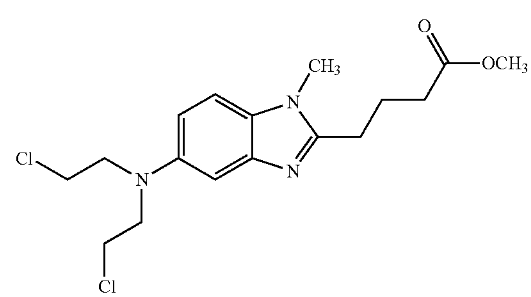 [SMILES: COC(=O)CCCc1nc2cc(N(CCCl)CCCl)ccc2n1C] |

TABLE-continued

HPLC Retention Times and Structures of Bendamustine Impurities

| Sr No | Name of Impurity | RT (min) | RRT | Structure |
|---|---|---|---|---|
| 4 | Bendamustine | 25 | 1.00 | 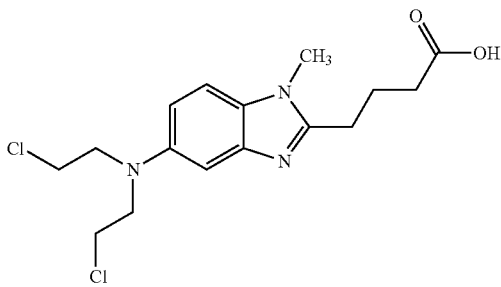 [SMILES: Cn1c(CCCC(=O)O)nc2cc(N(CCCl)CCCl)ccc21] |

20

TABLE

Impurities Chemical Name and specification justification

| ID | Chemical Name | % Limit | Justification |
|---|---|---|---|
| Related Compound-A | 4-{5-[Bis(2-hydroxyethyl) amino]-1-methyl-1H-benzimidazol-2-yl} butanoic acid | NMT 0.3% | USP monograph of Injection |
| Related Compound-B | 4-(1-Methyl-5-Morpholino-1H-benzimidazol-2-yl) butanoic acid | NMT 0.2% | USP monograph of Injection |
| Related Compound-C | Ethyl 4-{5-[bis(2-hydroxyethyl) amino]-1-methyl-1H-benzimidazol-2-yl} butanoate | NMT 0.20% | USP monograph of API |
| Related Compound-D | 4-{5-[(2-Chloroethyl) amino]-1-methyl-1H-benzimidazol-2-yl} butanoic acid | NMT 0.6% | USP monograph of Injection |
| Related Compound-E | 4-{5-[(2-Chloroethyl) (2-hydroxyethyl) amino]-1-methyl-1H-benzimidazol-2-yl} butanoic acid | NMT 1.5% | USP monograph of Injection |
| Related Compound-F | Mannitol-1-yl 4-{5-[bis(2-chloroethyl) amino]-1-methyl-1H-benzimidazol-2-yl} | NMT 0.5% | USP monograph of Injection |
| Related Compound-G | 4-[6-(2-Chloroethyl)-3,6,7,8-tetrahydro-3-methylimidazo[4,5-h] [1,4] benzothiazin-2-yl] butanoic acid | NMT 0.35% | USP monograph of API |
| Related Compound-H | 4-[5-({2-[(4-{5-[Bis(2-chloroethyl) amino]-1-methyl-1H-benzimidazol-2-yl} butanol) oxy] ethyl} (2-chloroethyl) amino)-1-methyl-1H-benzimidazol-2-yl] butanoic acid | NMT 0.9% | USP monograph of Injection |
| Related Compound-I | Ethyl 4-{5-[bis(2-chloroethyl) amino]-1-methyl-1H-benzimidazol-2-yl} butanoate | NMT 0.40% | USP monograph of API |
| Methyl Ester | Methyl 4-{5-[bis(2-chloroethyl) amino]-1-methyl-1H-benzimidazol-2-yl} butanoate | NMT 0.15% | As per API inhouse specification |

Example 1

Solubility of Bendamustine Hydrochloride in DMA-Water Mixture

To 10 ml of DMA-water mixture, excess (~2-3 g) of Bendamustine Hydrochloride hydrate was added and the mixture was stirred for 24 hr while keeping in a constant temperature bath. After 24 hr, the mixture was centrifuged to remove the undissolved solid and the supernatant was filtered through a 0.2 micron filter. The clear filtrate was assayed.

Results:

| Composition | Temperature | Solubility |
|---|---|---|
| DMA | 5° C. | 72 mg/mL |
| DMA:Water 97:3 | 5° C. | 116 mg/mL |
| DMA:Water 95:5 | 5° C. | 114 mg/mL |
| DMA:Water 90:10 | 5° C. | 201 mg/mL |
| DMA:Water 80:20 | 5° C. | 169 mg/mL |
| DMA:Water 60:40 | 5° C. | 67 mg/mL |

Example 2

Preparation of Bendamustine HCl Solution 90/mg/mL in DMA:Water (99:1)

A mixture of 99 mL of DMA and 1 mL of water was stirred until a clear solution was formed. This solution was degassed by passing $N_2$ for 30 min. In a 100 mL volumetric flask containing 80 mL of this solution 9.46 g of Bendamustine Hydrochloride hydrate was added and stirred until the solid dissolved (5-10 min). The solution was diluted to volume with additional degassed DMA-water and stirred for 5 min. The solution was filtered through a 0.2 micron filter and amber glass vials were filled with 1 ml of the filtrate. The vials were flushed with $N_2$ and sealed. The vials were kept on stability at and analyzed at various time points.

Example 3

Preparation of Bendamustine HCl Solution 90 mg/mL in DMA:Water (98:2)

A solution prepared from 98 mL DMA and 2 mL water was used to make a solution of Bendamustine HCl solution 90 mg/mL as described in Example 2.

Example 4

Preparation of Bendamustine HCl Solution 90 mg/mL in DMA:Water (97:3)

A solution prepared from 97 mL DMA and 3 mL water was used to make a solution of Bendamustine HCl solution 90 mg/mL as described in Example 2.

Example 5

Preparation of Bendamustine HCl Solution 180 mg/mL in DMA:Water (98:2)

A mixture of 98 mL of DMA and 2 mL of water was stirred until a clear solution was formed. This solution was degassed by passing N2 for 30 min. In a 100 mL volumetric flask containing 80 mL of this solution 18.43 g of Bendamustine Hydrochloride hydrate was added and stirred until the solid dissolved (5-10 min). The solution was diluted to volume with additional degassed DMA-water and stirred for 5 min. The solution was filtered through a 0.2 micron filter and amber glass vials were filled with 1 ml of the filtrate. The vials were flushed with N2 and sealed. The vials were kept on stability at and analyzed at various time points.

Example 6

Preparation of Bendamustine HCl Solution 100 mg/mL in DMA:Water (60:40)

Bendamustine Hydrochloride, hydrate (10.457 g) was added to 50 mL of degassed DMA and the mixture was stirred for 5 min until the solid dissolved. To this solution 40 ml of purified water was added with stirring. After through mixing the solution was diluted to 100 mL by adding DMA. The solution was stirred for an additional 5 min. and the resulting 100 ml solution of 100 mg/mL of Bendamustine Hydrochloride was used to fill 2 mL vials. The vials were flushed with N2, and sealed. The vials were kept on stability at various temperatures and analyzed at various time points.

Example 7

Solutions of Bendamustine Hydrochloride hydrate in DMA with varying amounts of water were prepared by adjusting the quantities of DMA and water and following the procedure of example 1.

Results for stability of solution formulations Bendamustine Hydrochloride hydrate 90-200 mg/mL in DMA/water are shown in Table 7.

TABLE 7

Stability of Bendamustine Hydrochloride hydrate 90-200 mg/mL in DMA/water

| | | | | Related Compounds (%) | | |
| --- | --- | --- | --- | --- | --- | --- |
| Formulation | Potency (mg/ml) | Stability Condition | Assay | 0.55 RRT DCE | 0.58 RRT Monohydroxyl | Total Impurity |
| DMA:Water 99:01 | 90 | Initial | 101.3 | 0.03 | 0.03 | 0.08 |
| | | 3M@5° C. | 100.7 | 0.03 | 0.03 | 0.06 |
| | | 6M@5° C. | 100.3 | 0.03 | 0.04 | 0.08 |
| | | 9M@5° C. | 98.1 | 0.04 | 0.04 | 0.13 |
| | | 12M@5° C. | 100 | 0.02 | 0.04 | 0.06 |
| DMA:Water 98:02 | 90 | Initial | 101.1 | 0.03 | 0.02 | 0.08 |
| | | 3M@5° C. | 100.4 | 0.02 | 0.04 | 0.06 |
| | | 6M@5° C. | 99.9 | 0.03 | 0.04 | 0.08 |
| | | 9M@5° C. | 98.8 | 0.03 | 0.04 | 0.08 |
| | | 12M@5° C. | 101 | 0.02 | 0.05 | 0.07 |
| DMA:Water 97:03 | 90 | Initial | 101.8 | 0.03 | 0.03 | 0.07 |
| | | 3M@5° C. | 101.7 | 0.02 | 0.04 | 0.06 |
| | | 6M@5° C. | 100.8 | 0.02 | 0.04 | 0.07 |
| | | 9M@5° C. | 98.8 | 0.03 | 0.04 | 0.07 |
| | | 12M@5° C. | 101 | 0.02 | 0.05 | 0.07 |
| DMA:Water 99:01 | 180 | Initial | 99.9 | 0.03 | 0.03 | 0.06 |
| | | 3M@5° C. | 101.3 | 0.02 | 0.04 | 0.06 |
| | | 6M@5° C. | 99.3 | 0.03 | 0.04 | 0.08 |
| | | 9M@5° C. | 100.6 | 0.02 | 0.04 | 0.12 |
| | | 12 M@5° C. | 100.4 | 0.03 | 0.04 | 0.08 |
| DMA:Water 98:02 | 180 | Initial | 100.6 | 0.03 | 0.03 | 0.07 |
| | | 3M@5° C. | 102.4 | 0.02 | 0.03 | 0.05 |
| | | 6M@5° C. | 100.8 | 0.02 | 0.06 | 0.06 |
| | | 9M@5° C. | 99.4 | 0.02 | 0.04 | 0.12 |
| | | 12M@5° C. | 101 | 0.03 | 0.04 | 0.08 |

TABLE 7-continued

Stability of Bendamustine Hydrochloride hydrate 90-200 mg/mL in DMA/water

| | | | | Related Compounds (%) | | |
|---|---|---|---|---|---|---|
| Formulation | Potency (mg/ml) | Stability Condition | Assay | 0.55 RRT DCE | 0.58 RRT Monohydroxyl | Total Impurity |
| DMA:Water 97:03 | 180 | Initial | 100.7 | 0.03 | 0.03 | 0.07 |
| | | 3M@5° C. | 99.9 | 0.04 | 0.02 | 0.06 |
| | | 6M@5° C. | 99.5 | 0.03 | 0.05 | 0.09 |
| | | 9M@5° C. | 98.3 | 0.02 | 0.04 | 0.11 |
| | | 12M@5° C. | 100.2 | 0.03 | 0.05 | 0.08 |
| DMA:Water 90:10 | 200 | Initial | 100.2 | 0.03 | 0.02 | 0.07 |
| | | 3M@5° C. | 101.9 | 0.02 | 0.05 | 0.06 |
| | | 6M@5° C. | 98.1 | 0.02 | 0.05 | 0.1 |
| | | 9M@5° C. | 100.2 | 0.02 | 0.06 | 0.13 |
| DMA:Water 90:10 | 100 | Initial | 100.3 | 0.1 | 0.04 | 0.14 |
| | | 3M@5° C. | 99.8 | 0.19 | 0.04 | 0.23 |
| DMA:Water 80:20 | 100 | Initial | 99.9 | 0.03 | 0.04 | 0.07 |
| | | 3M@5° C. | 101.8 | 0.09 | 0.06 | 0.15 |
| DMA:Water 75:25 | 100 | Initial | 97.7 | 0.04 | 0.03 | 0.11 |
| | | 3M@5° C. | 99.01 | 0.11 | 0.09 | 0.20 |
| DMA:Water 60:40 | 100 | Initial | 99.1 | 0.05 | 0.09 | 0.18 |
| | | 3M@5° C. | 98.9 | 0.07 | 0.46 | 0.67 |

Example 8: Preparation of Bendamustine HCl Solution 100 mg/mL in DMA:Water (97:3)

Composition

| Ingredients | Quantity | % w/v |
|---|---|---|
| Bendamustine Hydrocloride | 100 mg/mL | 10.0 |
| DMA:Water (97:3 v/v) | q.s to 1 mL | q.s to 100% |

A solution consisting of 97 mL of DMA and 3 mL of water was mixed. This solution was degassed by passing N2 for 120 min. Bendamustine Hydrochloride hydrate was added into 80% of final volume of the DMA/Water solution and stirred until the solid dissolved. The solution of Bendamustine in DMA/Water was diluted to batch volume. The Bendamustine solution was filtered and filled in a vial, purged with N2 and sealed. The sealed vials were kept on stability and analyzed at various time points.

Stability study Results are shown in Table 8

TABLE 8

Stability results for Bendamustine HCl solution 100 mg/mL in DMA:Water (97:3) degassed

| | Condition Specification | Initial | 12 M 5° C. | 6 M 25° C./60% RH | 12 M 25° C./60% RH | 18 M 25 C./60% RH |
|---|---|---|---|---|---|---|
| | | | | Result % w/w | | |
| Assay | 90-110% | 100.3 | 100.6 | NP | 98.7 | NP |
| Related Compounds | | | | | | |
| Related Compound-A | NMT 0.3% | <LOQ | <LOQ | <LOQ | <LOQ | <LOQ |
| Related Compound-B | NMT 0.2% | <LOQ | <LOQ | <LOQ | <LOQ | 0.01 |
| Related Compound-C | NMT 0.20% | <LOQ | <LOQ | <LOQ | <LOQ | <LOQ |
| Related Compound-D | NMT 0.6% | 0.01 | 0.01 | 0.07 | 0.23 | 0.30 |
| Related Compound-E | NMT 1.5% | <LOQ | <LOQ | 0.08 | 0.12 | 0.16 |
| Related Compound-F | NMT 0.5% | <LOQ | <LOQ | <LOQ | <LOQ | <LOQ |
| Related Compound-G | NMT 0.35% | 0.09 | 0.09 | 0.11 | 0.11 | 0.17 |
| Methyl Ester | NMT 0.15% | <LOQ | <LOQ | <LOQ | <LOQ | <LOQ |
| Related Compound-H | NMT 0.9% | <LOQ | <LOQ | <LOQ | <LOQ | 0.07 |
| Related Compound-I | NMT 0.40% | <LOQ | <LOQ | <LOQ | <LOQ | <LOQ |
| Any unspecified impurity | NMT 0.2% | ND | 0.02 | 0.02 | 0.04 | 0.08 |
| Total Impurities | NMT 3.5% | 0.10 | 0.14 | 0.28 | 0.53 | 0.81 |

3 M/5° C. was considered as initial.
NP: Not performed,
LOQ: Limit of Quantification,
ND: Not Detected

Example 9: Bendamustine HCl Solution 100 mg/mL in DMA:Water (97:3)

The composition and procedure of example 8 were followed.

Stability study Results are shown in Table 9.

TABLE 9

Stability results for Bendamustine HCl solution 100 mg/mL in DMA:Water (97:3) degassed

| | Condition Specification | Initial | 12 M 5° C. | 6 M 25° C./60% RH | 12 M 25° C./60% RH | 18 M 25 C./60% RH |
|---|---|---|---|---|---|---|
| | | | | Result % w/w | | |
| Assay | 90-110% | 102.9 | 99.3 | 99.3 | 101.1 | NP |
| Related Compounds | | | | | | |
| Related Compound-A | NMT 0.3% | <LOQ | <LOQ | <LOQ | <LOQ | <LOQ |
| Related Compound-B | NMT 0.2% | <LOQ | <LOQ | <LOQ | <LOQ | 0.01 |
| Related Compound-C | NMT 0.20% | <LOQ | <LOQ | <LOQ | <LOQ | <LOQ |
| Related Compound-D | NMT 0.6% | 0.01 | 0.01 | 0.02 | 0.07 | 0.20 |
| Related Compound-E | NMT 1.5% | <LOQ | <LOQ | 0.08 | 0.14 | 0.15 |
| Related Compound-F | NMT 0.5% | <LOQ | <LOQ | <LOQ | <LOQ | <LOQ |
| Related Compound-G | NMT 0.35% | 0.10 | 0.09 | 0.11 | 0.12 | 0.18 |
| Methyl Ester | NMT 0.15% | <LOQ | <LOQ | <LOQ | <LOQ | <LOQ |
| Related Compound-H | NMT 0.9% | <LOQ | <LOQ | <LOQ | <LOQ | 0.07 |
| Related Compound-I | NMT 0.40% | <LOQ | <LOQ | <LOQ | <LOQ | <LOQ |
| Any unspecified impurity | NMT 0.2% | 0.03 | 0.02 | 0.02 | 0.04 | 0.08 |
| Total Impurities | NMT 3.5% | 0.14 | 0.15 | 0.23 | 0.4 | 0.71 |

3 M/5° C. was considered as Initial.
NP: Not performed,
LOQ: Limit of Quantification

Example 10: Bendamustine HCl Solution 100 mg/mL in DMA:Water (97:3)

The composition and procedure of example 8 were followed.

Stability Study Results batch are shown in Table 10.

TABLE 10

Stability results for Bendamustine HCl solution 100 mg/mL in DMA:Water (97:3)

| | Condition Specification | Initial | 24M 25° C./ 60% RH |
|---|---|---|---|
| | | | Result % w/w |
| Assay | 90-110% | 101.0 | 102.4 |
| Related Compounds | | | |
| Related Compound-A | NMT 0.3% | <LOQ | <LOQ |
| Related Compound-B | NMT 0.2% | <LOQ | 0.02 |
| Related Compound-C | NMT 0.20% | <LOQ | <LOQ |
| Related Compound-D | NMT 0.6% | 0.01 | 0.59 |
| Related Compound-E | NMT 1.5% | <LOQ | 0.21 |
| Related Compound-F | NMT 0.5% | <LOQ | <LOQ |
| Related Compound-G | NMT 0.35% | 0.10 | 0.09 |

TABLE 10-continued

Stability results for Bendamustine HCl solution 100 mg/mL in DMA:Water (97:3)

| | Condition Specification | Initial | 24M 25° C./ 60% RH |
|---|---|---|---|
| | | | Result % w/w |
| Methyl Ester | NMT 0.15% | <LOQ | <LOQ |
| Related Compound-H | NMT 0.9% | <LOQ | 0.10 |
| Related Compound-I | NMT 0.40% | <LOQ | <LOQ |
| Any unspecified impurity | NMT 0.2% | 0.03 | 0.14 |
| Total Impurities | NMT 3.5% | 0.20 | 1.3 |

3 M/5° C. was considered as Initial,
LOQ: Limit of Quantification

Example 11: Bendamustine HCl Solution 100 mg/mL in DMA:Water (97:3)

The composition and procedure of example 8 were followed.

Stability study Results are shown in Table 11

TABLE 11

Stability results for Bendamustine HCl solution 100 mg/mL in DMA:Water (97:3)

| | Condition Specification | Initial | 6M 25° C./ 60% RH | 12M 25° C./ 60% RH | 18M 25° C./ 60% RH |
|---|---|---|---|---|---|
| | | | Result % w/w | | |
| Assay | 90-110% | 97.5 | NP | 100.9 | 101.1 |
| Related Compounds | | | | | |
| Related Compound-A | NMT 0.3% | <LOQ | <LOQ | <LOQ | ND |
| Related Compound-B | NMT 0.2% | <LOQ | <LOQ | <LOQ | ND |
| Related Compound-C | NMT 0.20% | <LOQ | <LOQ | <LOQ | <LOQ |
| Related Compound-D | NMT 0.6% | 0.01 | 0.02 | 0.05 | 0.15 |

TABLE 11-continued

Stability results for Bendamustine HCl solution 100 mg/mL in DMA:Water (97:3)

| | Condition Specification | Initial | 6M 25° C./ 60% RH | 12M 25° C./ 60% RH | 18M 25° C./ 60% RH |
|---|---|---|---|---|---|
| | | | Result % w/w | | |
| Related Compound-E | NMT 1.5% | <LOQ | 0.06 | 0.11 | 0.16 |
| Related Compound-F | NMT 0.5% | <LOQ | <LOQ | <LOQ | ND |
| Related Compound-G | NMT 0.35% | 0.09 | 0.13 | 0.16 | 0.18 |
| Methyl Ester | NMT 0.15% | <LOQ | <LOQ | <LOQ | ND |
| Related Compound-H | NMT 0.9% | <LOQ | <LOQ | 0.04 | 0.08 |
| Related Compound-I | NMT 0.40% | <LOQ | <LOQ | <LOQ | ND |
| Any unspecified impurity | NMT 0.2% | 0.01 | 0.02 | 0.05 | 0.09 |
| Total Impurities | NMT 3.5% | 0.11 | 0.25 | 0.43 | 0.69 |

NP: Not performed,
LOQ: Limit of Quantification

Example 12: Addition of Antioxidant

A control (12A) of Bendamustine HCl solution 100 mg/mL in DMA:Water (97:3) was prepared at the same time as solutions including Butylated hydroxytoluene as antioxidant (12B, 12C). The procedure of Example 8 was followed.

Batch 12-B

| Ingredients | Quantity | % |
|---|---|---|
| Bendamustine Hydrochloride | 100 mg/mL | 10.0 |
| Butylated hydroxytoluene | 0.5 mg/mL | 0.05 |
| DMA:Water (97:3) | q.s to 1 mL | q.s to 100% |

Batch 12-C

| Ingredients | Quantity | % |
|---|---|---|
| Bendamustine Hydrochloride | 100 mg/mL | 10.0 |
| Butylated hydroxytoluene | 0.05 mg/mL | 0.005 |
| DMA:Water (97:3) | q.s to 1 mL | q.s to 100% |

Stability study Results are shown in Tables 12A, 12B and 12C. NP: Not performed, LOQ: Limit of Quantification

TABLE 12A

Stability results for Example 12A Control Batch, Bendamustine HCl solution 100 mg/mL in DMA:Water (97:3)

| | Condition Specification | Initial | 6M 25° C./ 60% RH |
|---|---|---|---|
| Assay | 90-110% | 102.3 | 100.5 |
| Related Compounds | | | |
| Related Compound-A | NMT 0.3% | <LOQ | <LOQ |
| Related Compound-B | NMT 0.2% | <LOQ | <LOQ |
| Related Compound-C | NMT 0.20% | <LOQ | <LOQ |
| Related Compound-D | NMT 0.6% | 0.01 | 0.41 |
| Related Compound-E | NMT 1.5% | <LOQ | 0.09 |
| Related Compound-F | NMT 0.5% | <LOQ | <LOQ |
| Related Compound-G | NMT 0.35% | 0.09 | 0.10 |
| Methyl Ester | NMT 0.15% | <LOQ | <LOQ |
| Related Compound-H | NMT 0.9% | <LOQ | <LOQ |
| Related Compound-I | NMT 0.40% | <LOQ | <LOQ |
| Any unspecified impurity | NMT 0.2% | 0.03 | 0.04 |
| Total Impurities | NMT 3.5% | 0.13 | 0.70 |

TABLE 12B

Stability Results for Example 12B, Bendamustine HCl solution 100 mg/mL in DMA:Water (97:3) with 0.05% w/v BHT

| | Condition Specification | Initial | 6M 25° C./ 50% RH |
|---|---|---|---|
| Assay | 90-110% | 101.8 | 99.9 |
| Related Compounds | | | |
| Related Compound-A | NMT 0.3% | <LOQ | <LOQ |
| Related Compound-B | NMT 0.2% | <LOQ | <LOQ |
| Related Compound-C | NMT 0.20% | <LOQ | <LOQ |
| Related Compound-D | NMT 0.6% | 0.01 | 0.14 |
| Related Compound-E | NMT 1.5% | <LOQ | 0.09 |
| Related Compound-F | NMT 0.5% | <LOQ | <LOQ |
| Related Compound-G | NMT 0.35% | 0.09 | 0.11 |
| Methyl Ester | NMT 0.15% | <LOQ | <LOQ |
| Related Compound-H | NMT 0.9% | <LOQ | <LOQ |
| Related Compound-I | NMT 0.40% | <LOQ | <LOQ |
| Any unspecified impurity | NMT 0.2% | 0.03 | 0.02 |
| Total Impurities | NMT 3.5% | 0.13 | 0.39 |

TABLE 12C

Stability Results for Example 12B, Bendamustine HCl solution 100 mg/mL in DMA:Water (97:3) with 0.005% w/v BHT

| | Condition Specification | Initial | 6M 25° C./ 60% RH |
|---|---|---|---|
| Assay | 90-110% | 102.5 | 100.2 |
| Related Compounds | | | |
| Related Compound-A | NMT 0.3% | <LOQ | <LOQ |
| Related Compound-B | NMT 0.2% | <LOQ | <LOQ |
| Related Compound-C | NMT 0.20% | <LOQ | <LOQ |
| Related Compound-D | NMT 0.6% | 0.01 | 0.24 |
| Related Compound-E | NMT 1.5% | <LOQ | 0.09 |
| Related Compound-F | NMT 0.5% | <LOQ | <LOQ |
| Related Compound-G | NMT 0.35% | 0.09 | 0.10 |
| Methyl Ester | NMT 0.15% | <LOQ | <LOQ |
| Related Compound-H | NMT 0.9% | <LOQ | <LOQ |
| Related Compound-I | NMT 0.40% | <LOQ | <LOQ |
| Any unspecified impurity | NMT 0.2% | 0.03 | 0.02 |
| Total Impurities | NMT 3.5% | 0.13 | 0.50 |

Example 13: Comparative Stability

Linear extrapolation at room temperature of Experiments in the Figures of U.S. Patent Application Publication No. 2013/0210878 to Soppimath et al.

TABLE 13A

Stability of U.S. 2013/0210878 Examples

| No. | Composition of Product | Extrapolated Stability Duration | Mono-hydroxy Impurity | Total Impurity | Remark/Reference |
|-----|------------------------|---------------------------------|-----------------------|----------------|------------------|
| 1 | Bendamustine HCl in 90% propylene glycol, 10% water | 90 Days (3 months) at room temperature | 4.8% | 14.5% | Soppimath, FIG. 3 |
|   |   | 180 Days (6 months) at room temperature | 9.6% | 29.0% |   |
| 2 | Bendamustine HCl in 90% propylene glycol, 10% water, 175.3 mg sodium chloride | 90 Days (3 months) at room temperature | 1.4% | 4.3% | Soppimath, FIG. 2 |
|   |   | 180 Days (6 months) at room temperature | 2.8% | 8.6% |   |
| 3 | Bendamustine HCl in 75% propylene glycol, 25% water | 90 Days (3 months) at room temperature | 36% | 67% | Soppimath, FIG. 4 |
|   |   | 180 Days (6 months) at room temperature | 72% | ~100% |   |
| 4 | Bendamustine HCl in 75% propylene glycol, 25% water, 175.3 mg sodium chloride | 90 Days (3 months) at room temperature | 12.9% | 26.8% | Soppimath, FIG. 3 |
|   |   | 180 Days (6 months) at room temperature | 25.8% | 53.5% |   |
| 5 | Bendamustine HCl in 50% propylene glycol, 50% water, 175.3 mg sodium chloride | 90 Days (3 months) at room temperature | ~100% | ~100% | Soppimath, FIG. 3 |
|   |   | 180 Days (6 months) at room temperature | ~100% | ~100% |   |

The formulations of Soppimath et al. will not meet the current USP specifications for Bendamustine monohydroxy impurity and total impurities after three months.

Formulation X

A scaled-up version of Formulation X from U.S. Patent Application Publication No. 2013/0210878 was prepared and stability of the formulation was tested at 2-8° C. and 25° C. storage conditions.

| Ingredient | Quantity/mL | Quantity/batch | Observation |
|---|---|---|---|
| Bendamustine HCl | 5.0 mg | 500 mg† | Clear solution |
| Water | 0.25 mL | 25 mL |   |
| Propylene Glycol | 0.75 mL | 75 mL |   |

†Theoretical quantity

Stability results for Formulation X are shown in Table 13B.

TABLE 13B

Stability of Formulation 13X

|   | Initial | 17 Days 2-8° C. | 38 Days 2-8° C. | 17 Days 25° C. | 38 Days 25° C. |
|---|---|---|---|---|---|
| Assay % | 101.4% | 102.7% | 101.2% | 93.6% | 81.5% |
| Monohydroxy-BDN | <LOQ (0.05%) | 0.43% | 0.85% | 6.0% | 9.9% |
| Highest unknown (RRT) | 0.03% (RRT 1.07) | 0.26% (RRT 0.83) | 0.85% (RRT 0.74) | 3.7% (RRT0.83) | 6.2% (RRT 0.82) |
| Total Impurities | 0.05% | 0.78% | 1.6% | 11.3% | 21.4% |

Scaled-up versions of formulas X, XI, and XII from Table 5 in U.S. Patent Application Publication No. 2013/0210878 were prepared but replacing propylene glycol with DMA. The stability of the formulations was tested at 2-8° C. and 25° C. storage conditions.

Composition Formula X-DMA

| Ingredient | Quantity/mL | Quantity/batch | Observation |
|---|---|---|---|
| Bendamustine HCl | 5.0 mg | 500 mg† | Clear solution |
| Water | 0.25 mL | 25 mL | |
| Dimethylacetamide | 0.75 mL | 75 mL | |

†Theoretical quantity

Stability results for Formulation X-DMA are shown in Table 13C.

TABLE 13C

Stability of Formulation 13X-DMA

| Stability Condition | Initial | 17 Days 2-8° C. | 38 Days 2-8° C. | 17 Days 25° C. | 38 Days 25° C. |
|---|---|---|---|---|---|
| Assay % | 103.5% | 105.0% | 105.5% | 103.0% | 95.2% |
| Monohydroxy-BDN | <LOQ (0.05%) | 0.47% | 0.70% | 2.1% | 7.4% |
| Highest unknown (RRT) | 0.03% (RRT 1.07) | 0.02% (RRT 1.06) | 0.02% (RRT 0.58) | 0.03% (RRT 0.97) | 0.10% (RRT 0.98) |
| Total Impurities | 0.04% | 0.69% | 0.98% | 2.9% | 10.2% |

Composition Formula XI-DMA

| Ingredient | Quantity/mL | Quantity/batch | Observation |
|---|---|---|---|
| Bendamustine HCl | 5.0 mg | 500 mg† | Clear solution |
| Sodium Chloride | 14.61 mg | 1.461 gm | |
| Water | 0.25 mL | 25 mL | |
| Dimethylacetamide | 0.75 mL | 75 mL | |

†Theoretical quantity

Stability results for Formulation XI-DMA are shown in Table 13D

TABLE 13D

Stability of formulation 13XI-DMA

| Stability Condition | Initial | 17 Days 2-8° C. | 38 Days 2-8° C. | 17 Days 25° C./60% RH | 38 Days 25° C./60% RH |
|---|---|---|---|---|---|
| Assay % | 103.9% | 103.5% | 105.1% | 102.6% | 99.0% |
| Monohydroxy-BDN | <LOQ (0.05%) | 0.09% | 0.13% | 0.42% | 1.2% |
| Highest unknown (RRT) | 0.02% (RRT 1.07) | 0.02% (RRT 1.07) | 0.03% (RRT 1.09) | 0.08% (RRT 1.09) | 0.58% (RRT 0.10) |
| Total Impurities | 0.02% | 0.33% | 0.45% | 1.6% | 4.8% |

Composition Formula XII-DMA

| Ingredient | Quantity/mL | Quantity/batch | Observation |
|---|---|---|---|
| Bendamustine HCl | 5.0 mg | 500 mg† | Precipitation |
| Sodium Chloride | 29.22 mg | 2.922 gm | |
| Water | 0.25 mL | 25 mL | |
| Dimethylacetamide | 0.75 mL | 75 mL | |

†Theoretical quantity

Storage stability study was not conducted on Formulation XII-DMA due to the precipitation of the initial formulation.

When the propylene glycol in the most stable formulation from Table 5 of Soppimath (Formula XI) was replaced with DMA, precipitation occurred and a solution was not formed.

Example 14: Comparative Study

Trials (Trial 1-Trial 4) simulating compositions of Tables 16 and 18 of WO 2015/054550 to Anyarambhatla. The trial compositions were not lyophilized and were kept at 25° C./60% RH and 40° C./75% RH storage conditions. The stability was tested up to one (1) month. Stability test results for the trial batches are summarized in Tables 14A and 14B.

TABLE 14A

Compositions of Trials 1-4

| Ingredients | Quantity/Batch | | | |
|---|---|---|---|---|
| | Trial 1 | Trial 2 | Trial 3 | Trial 4 |
| Bendamustine HCl | 25.0 mg/mL | 25.0 mg/mL | 25.0 mg/mL | 15.0 mg/mL |
| Mannitol, USP | 42.5 mg/mL | 42.5 mg/mL | 42.5 mg/mL | 25.5 mg/mL |
| 100% DMSO | q.s. to 100 mL | — | — | q.s. to 100 mL |
| 90% DMSO in water | — | q.s. to 100 mL | — | — |
| 80% DMSO in water | — | — | q.s. to 100 mL | — |

TABLE 14B

Stability results of Trials 1-4

| Stability condition | Trial No./ Batch No. | Assay | Related Compounds (RC) Highest Unknown | Total impurities |
|---|---|---|---|---|
| Initial | Trial 1 | 100.8% | 0.02% (RRT 1.07) | 0.26% |
| | Trial 2 | 101.4% | 0.02% (RRT 1.07) | 0.60% |
| | Trial 3 | 100.6% | 0.02% (RRT 1.07) | 0.44% |
| | Trial 4 | 100.5% | 0.02% (RRT 1.07) | 0.27% |
| 2W/25° C./ 60% RH | Trial 1 | 98.4% | 0.02% (RRT 1.07) | 0.69% |
| | Trial 2 | 98.6% | 0.02% (RRT 1.07) | 2.0% |
| | Trial 3 | 98.1% | 0.02% (RRT 1.07) | 1.4% |
| | Trial 4 | 98.9% | 0.05% (RRT 0.72) | 0.64% |
| 1M/25° C./ 60% RH | Trial 1 | 99.1% | 0.04% (RRT 0.72) | 1.0% |
| | Trial 2 | 98.0% | 0.04% (RRT 0.72) | 2.9% |
| | Trial 3 | 97.5% | 0.05% (RRT 0.72) | 2.0% |
| | Trial 4 | 100.0% | 0.10% (RRT 0.72) | 1.0% |
| 1M/40° C./ 75% RH | Trial 1 | 96.4% | 0.06% (RRT 0.87) | 4.9% |
| | Trial 2 | 90.3% | 0.09% (RRT 0.72) | 13.1% |
| | Trial 3 | 92.4% | 0.10% (RRT 0.72) | 9.0% |
| | Trial 4 | 95.5% | 0.03% (RRT 0.72) | 4.4% |

Bendamustine compositions of Anyarambhatla do not achieve acceptable stability at 1 month under accelerated storage conditions (40° C./75% RH) without the need for lyophilization. On the other hand, the product of the present invention has significantly less degradation under the same storage conditions.

Stability results for Applicant's compositions with 100 mg/mL Bendamustine in 97% DMA and 3% water are shown in Table 14C.

TABLE 14C

Comparative Stability Results for Applicant's Composition

| Stability condition | Assay | Related Compounds (RC) Highest Unknown | Total Impurities |
|---|---|---|---|
| Initial | 103.7% | 0.02% | 0.14% |
| | 102.2% | 0.01% | 0.14% |
| 1M/40° C./75% RH | 99.9% | 0.02% | 0.3% |
| | 99.4% | 0.02% | 0.31% |

Total impurities in the compositions of Anyarambhatla are at least 2 to 4 times higher at initial stage and 14 to 42 times higher at 40° C. after 1 month of storage than Applicant's Bendamustine composition. Same degradation is expected at refrigerated conditions (2-8° C.) or room temperature (25° C.) through shelf-life of the product.

Example 15: Preparation of Bendamustine HCl Solution 100 mg/mL in DMA:Water (96:4)

Composition

| Ingredients | Quantity | % w/v |
|---|---|---|
| Bendamustine Hydrochloride | 100 mg/mL | 10.0 |
| Butylated hydroxytoluene | 0.018 mg/mL | 0.0018 |
| DMA:Water (96:4 v/v) | q.s to 1 mL | q.s to 100% |

A solution consisting of 96 mL of DMA and 4 mL of water was mixed. This solution was degassed by passing N2 for 120 min. Butylated hydroxytoluene was added. Bendamustine Hydrochloride hydrate was added into 80% of final volume of the DMA/Water solution and stirred until the solid dissolved. The solution of Bendamustine in DMA/Water was diluted to batch volume. The Bendamustine solution was filtered and filled in a vial, purged with N2 and sealed. The sealed vials were kept on stability and analyzed at various time points.

Stability study Results are shown in Table 15.

TABLE 15

Stability results for Bendamustine HCl solution 100 mg/mL in DMA:Water (96:4)

| | Condition Specification | Initial | 1M 25 C./60% RH | 1M/40 C./75% RH |
|---|---|---|---|---|
| | | Result % w/w | | |
| Assay | 90-110% | 103.5% | 102.2% | 102.4% |
| Related Compounds | | | | |
| Related Compound-A | NMT 0.3% | <LOQ | <LOQ | <LOQ |
| Related Compound-B | NMT 0.2% | <LOQ | <LOQ | 0.01 |
| Related Compound-C | NMT 0.20% | <LOQ | <LOQ | <LOQ |
| Related Compound-D | NMT 0.6% | <LOQ | <LOQ | 0.02 |
| Related Compound-E | NMT 1.5% | <LOQ | <LOQ | 0.11 |
| Related Compound-F | NMT 0.5% | <LOQ | <LOQ | <LOQ |
| Related Compound-G | NMT 0.35% | 0.11 | 0.12 | 0.12 |

TABLE 15-continued

Stability results for Bendamustine HCl solution 100 mg/mL in DMA:Water (96:4)

| | Condition Specification | Initial | 1M 25 C./60% RH | 1M/40 C./75% RH |
|---|---|---|---|---|
| | | | Result % w/w | |
| Assay | 90-110% | 103.5% | 102.2% | 102.4% |
| Methyl Ester | NMT 0.15% | <LOQ | <LOQ | <LOQ |
| Related Compound-H | NMT 0.9% | <LOQ | <LOQ | <LOQ |
| Related Compound-I | NMT 0.40% | <LOQ | <LOQ | <LOQ |
| Any unspecified impurity | NMT 0.2% | 0.03 | 0.02 | 0.06 |
| Total Impurities | NMT 3.5% | 0.15 | 0.15 | 0.40 |

Example 16: Preparation of Bendamustine HCl Solution 100 mg/mL in DMA:Water (94:6)

Composition

| Ingredients | Quantity | % w/v |
|---|---|---|
| Bendamustine Hydrochloride | 100 mg/mL | 10.0 |
| Butylated hydroxytoluene | 0.018 mg/mL | 0.0018 |
| DMA:Water (94:6 v/v) | q.s to 1 mL | q.s to 100% |

A solution consisting of 94 mL of DMA and 6 mL of water was mixed. This solution was degassed by passing N2 for 120 min. Butylated hydroxytoluene was added. Bendamustine Hydrochloride hydrate was added into 80% of final volume of the DMA/Water solution and stirred until the solid dissolved. The solution of Bendamustine in DMA/Water was diluted to batch volume. The Bendamustine solution was filtered and filled in a vial, purged with N2 and sealed. The sealed vials were kept on stability and analyzed at various time points.

Stability study Results are shown in Table 16.

TABLE 16

Stability for Bendamustine HCl solution 100 mg/mL in DMA: Water (94:6)

| | Condition Specification | Initial | 1M 25 C./60% RH | 1M/40 C./75% RH |
|---|---|---|---|---|
| | | | Result % w/w | |
| Assay | 90-110% | 103.9% | 101.3% | 103.2% |
| Related Compounds | | | | |
| Related Compound-A | NMT 0.3% | <LOQ | <LOQ | <LOQ |
| Related Compound-B | NMT 0.2% | <LOQ | <LOQ | 0.01 |
| Related Compound-C | NMT 0.20% | <LOQ | <LOQ | <LOQ |
| Related Compound-D | NMT 0.6% | <LOQ | <LOQ | 0.02 |
| Related Compound-E | NMT 1.5% | <LOQ | 0.05 | 0.15 |
| Related Compound-F | NMT 0.5% | <LOQ | <LOQ | <LOQ |
| Related Compound-G | NMT 0.35% | 0.12 | 0.12 | 0.12 |
| Methyl Ester | NMT 0.15% | <LOQ | <LOQ | <LOQ |
| Related Compound-H | NMT 0.9% | <LOQ | <LOQ | <LOQ |
| Related Compound-I | NMT 0.40% | <LOQ | <LOQ | <LOQ |
| Any unspecified impurity | NMT 0.2% | 0.03 | 0.02 | 0.07 |
| Total Impurities | NMT 3.5% | 0.16 | 0.2 | 0.42 |

Example 17: Preparation of Bendamustine HCl Solution 100 mg/mL in DMA:Water (92:8)

Composition

| Ingredients | Quantity | % w/v |
|---|---|---|
| Bendamustine Hydrochloride | 100 mg/mL | 10.0 |
| Butylated hydroxytoluene | 0.018 mg/mL | 0.0018 |
| DMA:Water (92:8 v/v) | q.s to 1 mL | q.s to 100% |

A solution consisting of 92 mL of DMA and 8 mL of water was mixed. This solution was degassed by passing N2 for 120 min. Butylated hydroxytoluene was added. Bendamustine Hydrochloride hydrate was added into 80% of final volume of the DMA/Water solution and stirred until the solid dissolved. The solution of Bendamustine in DMA/Water was diluted to batch volume. The Bendamustine solution was filtered and filled in a vial, purged with N2 and sealed. The sealed vials were kept on stability and analyzed at various time points.

Stability study Results are shown in Table 17.

TABLE 17

Stability results for Bendamustine HCl solution 100 mg/mL in DMA: Water (92:8)

|  | Condition Specification | Initial | 1M 25 C./60% RH | 1M/40 C./75%/RH |
|---|---|---|---|---|
|  |  | Result % w/w | | |
| Assay | 90-110% | 102.9% | 102.3% | 102% |
| Related Compounds | | | | |
| Related Compound-A | NMT 0.3% | <LOQ | <LOQ | <LOQ |
| Related Compound-B | NMT 0.2% | <LOQ | <LOQ | 0.01 |
| Related Compound-C | NMT 0.20% | <LOQ | <LOQ | <LOQ |
| Related Compound-D | NMT 0.6% | <LOQ | <LOQ | 0.02 |
| Related Compound-E | NMT 1.5% | <LOQ | 0.05 | 0.2 |
| Related Compound-F | NMT 0.5% | <LOQ | <LOQ | <LOQ |
| Related Compound-G | NMT 0.35% | 0.11 | 0.12 | 0.12 |
| Methyl Ester | NMT 0.15% | <LOQ | <LOQ | <LOQ |
| Related Compound-H | NMT 0.9% | <LOQ | <LOQ | 0.04 |
| Related Compound-I | NMT 0.40% | <LOQ | <LOQ | <LOQ |
| Any unspecified impurity | NMT 0.2% | 0.03 | 0.02 | 0.08 |
| Total Impurities | NMT 3.5% | 0.15 | 0.2 | 0.54 |

Example 18: Preparation of Bendamustine HCl Solution 100 mg/mL in DMA:Water (88:12)

Composition

| Ingredients | Quantity | % w/v |
|---|---|---|
| Bendanimustine Hydrochloride | 100 mg/mL | 10.0 |
| Butylated hydroxytoluene | 0.018 mg/mL | 0.0018 |
| DMA:Water (88:12 v/v) | q.s to 1 mL | q.s to 100% |

A solution consisting of 88 mL of DMA and 12 mL of water was mixed. This solution was degassed by passing N2 for 120 min. Butylated hydroxytoluene was added. Bendamustine Hydrochloride hydrate was added into 80% of final volume of the DMA/Water solution and stirred until the solid dissolved. The solution of Bendamustine in DMA/Water was diluted to batch volume. The Bendamustine solution was filtered and filled in a vial, purged with N2 and sealed. The sealed vials were kept on stability and analyzed at various time points.

Stability study results are shown in Table 18.

TABLE 18

Stability results for Bendamustine HCl solution 100 mg/mL in DMA:Water

|  | Condition Specification | Initial | 1M 25 C./60% RH | 1M/40 C./75% RH |
|---|---|---|---|---|
|  |  | Result % w/w | | |
| Assay | 90-110% | 102.8% | 102.6% | 102.5% |
| Related Compounds | | | | |
| Related Compound-A | NMT 0.3% | <LOQ | <LOQ | <LOQ |
| Related Compound-B | NMT 0.2% | <LOQ | <LOQ | 0.02 |

TABLE 18-continued

Stability results for Bendamustine HCl solution 100 mg/mL in DMA:Water

| | Condition Specification | Initial | 1M 25 C./60% RH | 1M/40 C./75% RH |
|---|---|---|---|---|
| | | | Result % w/w | |
| Assay | 90-110% | 102.8% | 102.6% | 102.5% |
| Related Compound-C | NMT 0.20% | <LOQ | <LOQ | <LOQ |
| Related Compound-D | NMT 0.6% | <LOQ | <LOQ | 0.02 |
| Related Comound-E | NMT 1.5% | <LOQ | 0.07 | 0.4 |
| Related Compound-F | NMT 0.5% | <LOQ | <LOQ | <LOQ |
| Related Compound-G | NMT 0.35% | 0.11 | 0.12 | 0.12 |
| Methyl Ester | NMT 0.15% | <LOQ | <LOQ | <LOQ |
| Related Compound-H | NMT 0.9% | <LOQ | <LOQ | 0.08 |
| Related Compound-I | NMT 0.40% | <LOQ | <LOQ | <LOQ |
| Any unspecified impurity | NMT 0.2% | 0.03 | 0.02 | 0.12 |
| Total Impurities | NMT 3.5% | 0.15 | 0.23 | 0.88 |

The liquid pharmaceutical formulations disclosed herein are advantageously stable at room temperature storage for at least 3 months and can be made with three ingredients (Bendamustine, water and DMA) and, optionally, stabilizer/antioxidant. The compositions have unexpectedly demonstrated significant stabilization of Bendamustine HCl in DMA and water mixture without adding salt or polyols. The liquid formulations always remain a solution (even during storage) and thus, are ready for use or ready for further dilution. They do not need to be lyophilized to be stable and thus, are never freeze dried and do not need to be reconstituted before use.

The pharmaceutical formulations disclosed herein can be used for any condition that is sensitive to treatment with Bendamustine, such as neoplastic diseases. Accordingly, the present invention also provides a method of treating a neoplastic disease in mammals, which comprises the steps of: diluting a pharmaceutical composition of the present invention, and administering an effective amount of said diluted pharmaceutical composition to a mammal in need thereof. The neoplastic disease may be leukemia or Hodgkin's disease.

The term "effective amount," as used herein, refers to the amount determined to be required to produce the physiological effect intended and associated with a given drug, as measured according to established pharmacokinetic methods and techniques, for the given administration route. Appropriate and specific therapeutically effective amounts can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration.

The liquid formulations of Bendamustine described herein are intended to be administered via injection, for example, they may be administered subcutaneously, intracutaneously, intravenously, intramuscularly, intra-articularly, intrasynovially, intrasternally, intrathecally, intralesionally, intracranially or via infusion. In a typical preparation, the volume of the liquid formulation of the present invention needed for the required dose can be aseptically withdrawn and transferred to an infusion bag of 0.9% Sodium Chloride (or other pharmaceutically acceptable intravenous solution) for injection. After transfer, the contents of the infusion bag are thoroughly mixed. Administration by intravenous infusion is typically provided over a time period of from about 30 to about 60 minutes. Previously described lyophilized formulations of Bendamustine required reconstitution of the lyophilized Bendamustine prior to mixture with the acceptable intravenous solution before infusion.

It is envisioned that the pharmaceutical formulations and preparations of the present invention can be administered in combination with one or more anti-neoplastic agents where the anti-neoplastic agent is given prior to, concurrently with, or subsequent to the administration of the formulation or preparation of the present invention. Pharmaceutically acceptable anti-neoplastic agents are known in the art.

It should be noted that the invention in its broader aspects is not limited to the specific details, representative compositions, methods, and processes, and illustrative examples described in connection with the preferred embodiments and preferred methods. Modifications and equivalents will be apparent to practitioners skilled in this art and are encompassed within the spirit and scope of the appended claims.

What is claimed is:

1. A ready to use or ready to dilute for use, stable liquid Bendamustine solution consisting essentially of:
    about 90 to about 200 mg/mL Bendamustine Hydrochloride or a hydrate form thereof,
    about 0.01 to about 0.5 mg/mL antioxidant, and
    a co-solvent consisting of about 1% v/v to about 12% v/v water and about 88% v/v to about 99% v/v N,N-Dimethylacetamide (DMA),
    the liquid Bendamustine solution being stable without the need for lyophilization, and wherein the formulation contains no less than about 98% of the amount of the Bendamustine Hydrochloride or a hydrate form thereof upon analysis by HPLC at initial testing and after 3 months at room temperature.

2. The Bendamustine solution of claim 1, wherein the Bendamustine Hydrochloride or a hydrate form thereof is Bendamustine HCl monohydrate.

3. The Bendamustine solution of claim 1, wherein the concentration of Bendamustine Hydrochloride or a hydrate form thereof is about 100 mg/m L.

4. The Bendamustine solution of claim 1, wherein the cosolvent consists of about 2% v/v to about 6% v/v water.

5. The Bendamustine solution of claim 1, wherein the cosolvent consists of 3% v/v water and 97% v/v DMA.

6. The Bendamustine solution of claim 1, wherein the antioxidant concentration is about 0.05 mg/mL.

7. The Bendamustine solution of claim 1, wherein the antioxidant concentration is about 0.018 mg/mL.

8. The Bendamustine solution of claim 1, wherein the antioxidant concentration is about 0.5 mg/mL.

9. The Bendamustine solution of claim 1, wherein the co-solvent is degassed with nitrogen.

10. The Bendamustine solution of claim 1, wherein the antioxidant is butylated hydroxytoluene.

11. A pharmaceutically acceptable, sealed vial containing:
a ready to use or ready to dilute for use, stable Bendamustine solution consisting of:
about 10% w/v Bendamustine Hydrochloride or a hydrate thereof;
about 0.001 w/v to about 0.05% w/v antioxidant;
a cosolvent consisting of about 1% v/v to about 12% v/v water and about 88% v/v to about 99% v/v N,N-Dimethylacetamide (DMA); and
nitrogen;
wherein the Bendamustine solution is stable without the need for lypholization.

12. The pharmaceutically acceptable, sealed vial of claim 11, wherein the antioxidant is butylated hydroxytoluene.

13. The pharmaceutically acceptable, sealed vial of claim 11 comprising 90-200 mg/mL Bendamustine Hydrochloride or a hydrate thereof.

14. A pharmaceutically acceptable, ready to use or ready to dilute for use, stable liquid Bendamustine composition comprising:
about 10% w/v Bendamustine Hydrochloride or a hydrate thereof; and
a cosolvent consisting of about 1% v/v to about 12% v/v water and about 88% v/v to about 99% v/v N,N-Dimethylacetamide (DMA),
wherein the composition is stable without the need for lyophilization, and substantially free of sodium chloride and/or polyols.

15. The liquid composition of claim 14, further comprising a stabilizer.

16. The liquid composition of claim 15, wherein the stabilizer is an antioxidant.

17. The liquid composition of claim 16, wherein the antioxidant is butylated hydroxytoluene.

18. A method of treating leukemia or Hodgkin's disease by administering an effective amount of a ready to use or ready to dilute for use, stable liquid Bendamustine solution consisting essentially of:
about 90 to about 200 mg/mL Bendamustine Hydrochloride or a hydrate form thereof,
about 0.01 to about 0.5 mg/mL antioxidant, and
a co-solvent consisting of about 1% v/v to about 12% v/v water and about 88% v/v to about 99% v/v N,N-Dimethylacetamide (DMA),
the liquid Bendamustine solution being stable without the need for lyophilization, and wherein the formulation contains no less than about 98% of the amount of the Bendamustine Hydrochloride or a hydrate form thereof upon analysis by HPLC at initial testing and after 3 months at room temperature.

19. A ready to use or ready to dilute for use, stable liquid Bendamustine solution consisting essentially of:
about 90 to about 200 mg/mL Bendamustine Hydrochloride or a hydrate form thereof, and
a co-solvent consisting of about 1% v/v to about 12% v/v water and about 88% v/v to about 99% v/v N,N-Dimethylacetamide (DMA),
the liquid Bendamustine solution being stable without the need for lyophilization, and wherein the formulation contains no less than about 98% of the amount of the Bendamustine Hydrochloride or a hydrate form thereof upon analysis by HPLC at initial testing and after 3 months at room temperature.

* * * * *